United States Patent
Volonte' et al.

(10) Patent No.: US 6,559,148 B1
(45) Date of Patent: May 6, 2003

(54) USE OF P₂Y PURINORECEPTOR ANTAGONIST FOR THE TREATMENT OF ISCHEMIA REPERFUSION

(75) Inventors: Cinzia Volonte', Rome (IT); Giuseppe Sancesario, Rome (IT); Giorgio Bernardi, Rome (IT)

(73) Assignees: Consiglio Nazionale delle Ricerche, Rome (IT); Fondazione Santa Lucia, Rome (IT)

( * ) Notice: Subject to any disclaimer, the term of this patent is extended or adjusted under 35 U.S.C. 154(b) by 0 days.

(21) Appl. No.: 09/857,344

(22) PCT Filed: Nov. 23, 1999

(86) PCT No.: PCT/EP99/08999
§ 371 (c)(1),
(2), (4) Date: Sep. 19, 2001

(87) PCT Pub. No.: WO00/32198
PCT Pub. Date: Jun. 8, 2000

(30) Foreign Application Priority Data

Dec. 2, 1998 (IT) .......................................... MI98A2613

(51) Int. Cl.⁷ ...................... A61K 31/53; A61K 31/675; A61K 31/52
(52) U.S. Cl. ...................... 514/245; 514/81; 514/263.4
(58) Field of Search .............................. 514/245, 263.3, 514/266, 263, 171, 210.04

(56) References Cited

U.S. PATENT DOCUMENTS 5,733,916 A * 3/1998 Neely .......................... 514/262

FOREIGN PATENT DOCUMENTS

| WO | WO 95/26728 | * 10/1995 |
| WO | WO 97/04760 | * 2/1997 |
| WO | WO 98/03178 | * 1/1998 |

OTHER PUBLICATIONS

"alteration in cardiac sarcolemmal atp receptors by oxyradicals", Musat et al, Ann. N.Y. Acad. Sci. 1996, 793(myocardial preservation), abstract.*

"p2 purinoceptor–mediated dilations in the rat middle cerebral artery after ischemia–reperfusion", Marrelli et al., american Journal of physiology, 1999, 276 (1 pt 2) h33–41, abstract.*

Volonte C et al: "Selected P2 Purinoceptor Modulators Prevent Glutamate–Evoked Cytotoxicity in Cultured Cerebellar Granule Neurons" Journal of Neuroscience Research,US,Wiley–Liss, vol. 45, No. 2, Jul. 15, 1996, pp. 183–193, XP002048687 ISSN: 0360–4012.

Burnstock G.: "Hypoxia, endothelium, and purines." Drug Development Research, (1993) 28/3 (301–305)., XP000892583.

Dunwiddie T V (Reprint) et al: "Purinoceptors in the central nervous system" Drug Development Research, (Nov.–Dec. 1996) vol. 39, No. 3–4, pp. 361–370. Publisher Wiley–Liss, Div John Wiley & Sons Inc, 605 Third Ave, New York NY 10158–0012. ISSN: 0272–4391., XP000892584 Univ Milan, Inst Pharmacol Sci, Via Balzaretti 9, I–20133 Milan, Italy (Reprint).

Sigma–Aldrich Certificate of Analysis: Product No. R115, Product Name: Reactive Blue 2.

Product Descriptin from Sigma–Aldrich catalog of Product No.: R115, Product Name: Reactive Blue 2.

* cited by examiner

Primary Examiner—Zohreh Fay
Assistant Examiner—Brian-Yong Kwon
(74) Attorney, Agent, or Firm—Millen, White, Zelano & Branigan, P.C.

(57) ABSTRACT

Use of compounds modulating P2 purinoceptors, in particular antagonists such as Basilen Blue E-3G (Reactive Blue 2), for the prevention of the damages due to global cerebral ischemia and ischemia-reperfusion. Said compounds reduce the mortality in case of global cerebral ischemia as well as the neuronal damage of the hippocampus.

2 Claims, 1 Drawing Sheet

USE OF P$_2$Y PURINORECEPTOR ANTAGONIST FOR THE TREATMENT OF ISCHEMIA REPERFUSION

This application is a 371 of PCT/EP99/08999, filed Nov. 23, 1999 published as WO 00/32198, Jun. 8, 2000.

OBJECT OF THE INVENTION

The present invention relates to the use of a specific class of compounds for the prevention of damages and mortality caused by global cerebral ischemia and ischemia-reperfusion and for the treatment of acute and chronic cerebrovascular diseases.

STATE OF THE ART

When cerebral blood flow is reduced to about 10–20% of the normal flow, neurons and astrocytes consume their cellular energy metabolites and lose their capacity of regulating transmembrane ionic gradients (Hansen A. J., *Physiol. Rev.* 1985; 65:101–148). As a consequence, ionic homeostasis results to be jeopardized and all types of cells degenerate, as a consequence of the ischemic infarction (Ginsberg M., *The Neuroscientist*, 1995; 1:95–103). It has been estimated in rodents that a cerebral ischemic injury reaches its peak 4–8 hours after the arterial occlusion, but it is possible to reduce the extent of the infarction without changing the duration or the intensity of the insult. As a matter of fact, the ischemic injury can be alleviated by the modulation of a wide range of parameters, such as: closing calcium channels associated to NMDA receptor (Siesjo B. et al., *Ann. Thorac. Surg.* 1995; 59:1316–1320); reducing intracellular free calcium (Tymianski M. et al., *Neuron* 1993; 11:221–235); reducing production of free radicals (Chan P., *Brain Pathol.* 1994; 59–65); lowering brain temperature (Dietrich W. et al., *Cellular and molecular mechanism of ischemic brain damage.* Siesjo B., Wieloch T., eds., 177–198. Philadelphia: Lippincott-Raven).

Adenosine, an endogenous nucleoside that binds to purinoceptors of P$_1$ type, exerts a neuromodulating activity in several areas of the central nervous system of mammals. It is moreover involved in the regulation of cerebral blood flow (Rudolphi K. A. et al., *Cerebrovascular brain metabolism reviews*, 1992; 4:346–369; Rudolphi K. A. et al., *Trends in Pharmacol. Sci.* 1992; 13:439–445; Fredholm B. B., *Neuroprotective agents and cerebral ischemia*, Green A. R., Cross A. J. eds., pp. 259–280, Academic Press 1997, San Diego). Adenosine acts as a neuroprotective agent during the onset of cerebral ischemic damage. It uses several mechanisms such as, for instance: inhibition of the neuronal activity by the reduction of both the excitatory amino acid release and the calcium ion influx; stabilization of the membrane potential by hyperpolarization; inhibition of the free radicals production; increase in blood supply by vasodilatation; inhibition of platelet aggregation and adhesion of neutrophils to endothelial cells (Miller, L. P., Hsu C., *J. of Neurotrauma*, 1992; 9:S563–S577; Rudolphi K. A. et al., *Trends in Pharmacol. Sci.* 1992; 13:439–445).

Unlike the direct involvement of P$_1$purinoceptors in the neuroprotective action played by adenosine, as at today little is known about a potential role of P$_2$ purinoceptors (preferred for ATP; Burnstock G.; *Neuropharmacology* 1997; 36, 11427–1139) in the onset or protection from cerebral ischemic damage.

U.S. Pat. No. 5,733,916 describes a method for the treatment of the damages caused by ischemia-reperfusion in organs intended for transplant or surgery. This method concerns the administration of an antagonist of the A1 adenosine receptor and/or an antagonist of P$_2$ purinoceptors. In particular, said antagonist for P$_2$ receptors is PPADS, utilized in described cases of lung ischemia. U.S. Pat. No. 5,733,916 concerns ischemia-reperfusion and in particular lung ischemia, which affects an organ that requires a drastic reduction in the blood supply, when it is subjected to transplant or surgery. Such drastic reduction causes ischemic damages that may be localized and severe. According to what is reported in U.S. Pat. No. 7,733,916, such damages are advantageously treated by administering PPADS (15 mg/kg) 30 minutes before ischemia, and/or an antagonist of the A1 adenosine receptor. U.S. Pat. No. 5,733,916 describes intravenous administration of PPADS, which allows the compound to reach the lung wherein ischemia has taken place.

OBJECTS OF THE INVENTION

Object of this invention is to provide a class of compounds that allow to reduce the damages and the mortality caused by cerebral ischemic injury and reperfusion-induced ischemia, with the ensuing possibility of an effective treatment of acute and chronic cerebrovascular diseases.

Another object of this invention is to provide a class of compounds allowing to modulate several physiological functions, for instance energy metabolism, neuronal activity, cell survival.

Another object of the present invention is to provide a class of compounds allowing to prevent the mortality caused by ischemic stress either induced or suffered. Another object of the present invention is to provide a class of compounds allowing to reduce mortality caused by cerebral ischemic insult and such as to be easily administered and to pass the blood-brain barrier. Still another object of the present invention is to provide a class of compounds representing a valid pharmacological alternative to agents that are already used for the treatment of ischemic insult, reperfusion and acute and chronic cerebrovascular diseases, either induced or suffered.

DESCRIPTION OF THE INVENTION

These and still other objects and related advantages, which will be better clarified by the following description, are achieved by the utilization of compounds that modulate P$_2$ purinoceptors, for the prevention of the damages and the mortality induced by global cerebral ischemia and ischemia-reperfusion. In particular, according to the present invention, the compound Basilen Blue E-3G (Reactive Blue 2), an antagonist of P2Y receptors, is advantageously employed for the prevention of damages and mortality induced by global cerebral ischemia and ischemia-reperfusion. The compound Basilen Blue, produced by Sigma, is commercially available, and the structure formula as well as its main chemical-physical characteristic is reported in the 1998 catalogue distributed in Italy by the Sigma Company (p. 165).

Always according to the present invention, the compounds that modulate P$_2$ purinoceptors, and in particular Basilen Blue, proved to be very effective when used in the treatment of cerebrovascular diseases. Said compounds proved to be very effective also as modulators of many physiological functions such as, for instance, energy metabolism, neuronal activity, cell survival.

Again, always according to the present invention, the compounds that modulate P$_2$ purinoceptors, in particular Basilen Blue, proved to be very effective when used as pharmacological tools for the prevention of mortality induced by cerebral ischemia and ischemia-reperfusion. They are a valid pharmacological alternative to agents that are already used for the treatment of ischemic insult, reperfusion and acute and chronic cerebrovascular diseases According to the present invention, the compounds that modulate $P_2$ purinoceptors are advantageously used in the prevention and treatment of cerebral damage caused by surgery to the carotid arteries, aorta, heart, brain, medulla spinalis, as well as in the prevention and treatment of hypovolemic brain ischemia, abdomen aneurysm, hypotension.

By way of non-limiting example of the present invention, some experimental examples are given herein that show the effectiveness of the compounds modulating $P_2$ purinoceptors, and in particular Basilen Blue, in the reduction of mortality induced by global ischemia. In particular, for such analysis Wistar albino adult male rats weighting 220–250 g have been utilized. Basilen Blue was diluted in saline solution. After a 12 hour fast, transient cerebral ischemia was induced in the rats by the Pulsinelli and Brierley method (*Stroke*, 10:267–272, 1979). The animals were anesthetized with 2% halotane in a mixture of 30% $O_2$ and 70% $N_2O$. Both vertebral arteries were electrically cauterized and thin claps from Teflon were loosely and reversibly placed around the common carotid arteries. The animals were allowed to recover from anesthesia and kept one per cage, under standard conditions of humidity, temperature and light. The following day, the rats were submitted to a mild anesthesia always with halothane and the claps previously placed around the common carotid arteries were tightened to produce the occlusion of 4 vessels (4-VO) for 30 minutes (in 24 animals). The absence of locomotion activity, the loss of corneal and righting reflexes and the presence of paralytic mydriasis, which took place after 1–2 minutes from the carotid occlusion, were the criteria according to which the animals were considered ischemic and included in the study. The rectal temperature was monitored during the following recovery period and kept constant at a temperature between 36.5 and 37° C. until the rats recovered the locomotion activity and the thermal homeostasis.

Immediately before the occlusion of the carotids, the animals were randomly assigned to two different groups.

One group was treated with two doses of Basilen Blue: the first dose (4,5 mg Basilen Blue/kg of body weight) was administered by intraperitoneal injection, 15 minutes before the carotid occlusion. The second dose (4,5 mg Basilen Blue/kg of body weight) was also administered by intraperitoneal injection, but 3 hours after the carotid occlusion. Basilen Blue was administered intraperitoneally at the above-described concentrations, which assure the passage through the blood-brain barrier. The animals belonging to the second group were instead treated with two doses of saline solution (at a total volume corresponding to that of Basilen Blue), administered exactly according to the above described method.

The animals submitted to 30 minutes of global cerebral ischemia remained motionless for about 6–8 hours after the removal of the carotid occlusion, but many of them showed a slow recovery of the locomotion activity. However, many animals suffered a progressive deterioration of their clinical condition, showing breathing disturbances and seizures, and eventually died within two days from the carotid occlusion.

In particular, following 30 minutes of global ischemia, 5 out of the 11 animals belonging to, the control group died, while only 3 out of the 13 animals belonging to the Basilen Blue-treated group died. The mortality index was therefore significantly lower in the animals treated with Basilen Blue compared to those of the control group (p>0,05). Also the neuronal damage to the hippocampus of the animals treated with Basilen Blue was less severe, with fewer neurons lost in the CA1–CA2 sectors.

Figure 1:
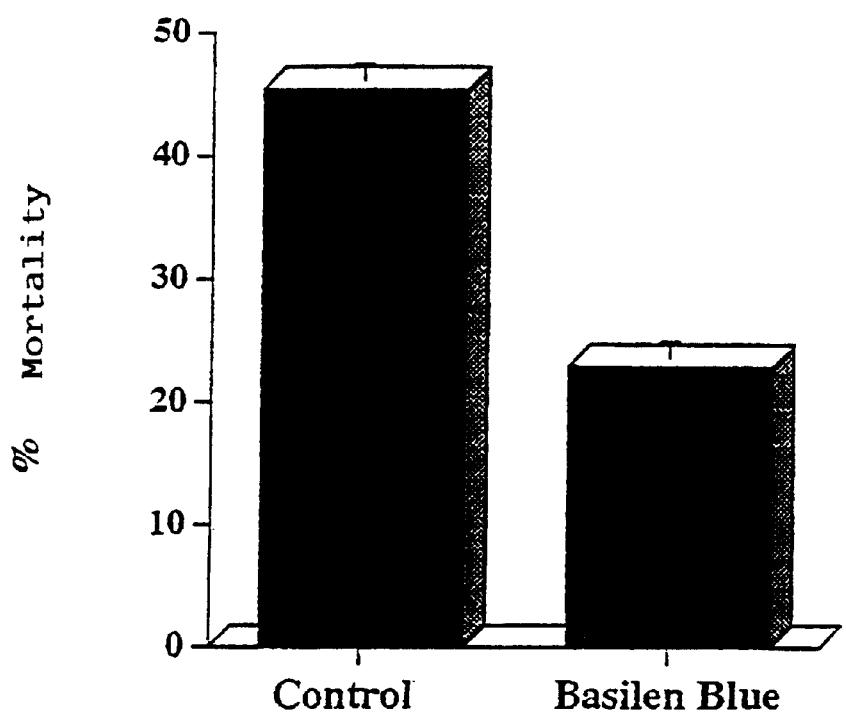
FIG. 1/1: Basilen Blue reduces the mortality of rats submitted to global cerebral ischemia.

Wistar albino male rats, having a mean weight of 220–250 g, treated with saline solution (controls) or Basilen Blue were submitted for 30 minutes to global cerebral ischemia, the whole as described previously. The mortality was then monitored for two days following the carotid occlusion in a total of 24 animals (11 controls and 13 treated with Basilen Blue). The experimental values represent the % of dead animals ±SEM (control: n=11; treated with Basilen Blue: n=13).

What is claimed is:

1. A method for treating a patient with ischemia reperfusion comprising administering a therapeutically effective amount of a compound which is a $P_2Y$ purinoreceptor antagonist.

2. A method for treating a patient with ischemia reperfusion comprising administering a therapeutically effective amount of Basilen Blue.

* * * * *